(12) United States Patent
Birkenbach

(10) Patent No.: US 7,527,387 B2
(45) Date of Patent: May 5, 2009

(54) MEDICAL MARKER MEANS

(75) Inventor: Rainer Birkenbach, Aufkirchen (DE)

(73) Assignee: BrainLAB AG, Feldkirchen (DE)

( * ) Notice: Subject to any disclaimer, the term of this patent is extended or adjusted under 35 U.S.C. 154(b) by 185 days.

(21) Appl. No.: 11/539,681

(22) Filed: Oct. 9, 2006

(65) Prior Publication Data

US 2007/0263375 A1    Nov. 15, 2007

Related U.S. Application Data

(60) Provisional application No. 60/738,546, filed on Nov. 21, 2005.

(30) Foreign Application Priority Data

Oct. 7, 2005   (EP) ................... 05021914

(51) Int. Cl.
   *F21K 2/00* (2006.01)
(52) U.S. Cl. .......................... 362/34; 362/84
(58) Field of Classification Search ............ 362/34, 362/84; 600/317
   See application file for complete search history.

(56) References Cited

U.S. PATENT DOCUMENTS

| | | | |
|---|---|---|---|
| 3,800,132 A | 3/1974 | Postal | |
| 4,015,111 A | 3/1977 | Spector | |
| 4,193,109 A * | 3/1980 | Heffernan et al. | 362/34 |
| 5,350,391 A | 9/1994 | Iacovelli | |
| 5,377,676 A * | 1/1995 | Vari et al. | 600/317 |
| 5,508,893 A * | 4/1996 | Nowak et al. | 362/34 |
| 5,626,134 A * | 5/1997 | Zuckerman | 600/317 |
| 5,860,845 A | 1/1999 | Goyhrach | |
| 6,485,158 B1 | 11/2002 | Bisotto | |
| 6,782,289 B1 | 8/2004 | Strauss | |
| 7,052,167 B2 * | 5/2006 | Vanderschuit | 362/572 |
| 2002/0151784 A1 | 10/2002 | Mizoguchi et al. | |
| 2003/0180800 A1 | 9/2003 | Lee et al. | |
| 2004/0246700 A1 * | 12/2004 | Palmer et al. | 362/34 |

FOREIGN PATENT DOCUMENTS

| | | |
|---|---|---|
| DE | 196 39 615 | 4/1998 |
| JP | 2005-011538 | 1/2005 |
| WO | 00/39576 | 7/2000 |
| WO | 01/47438 | 7/2001 |

* cited by examiner

*Primary Examiner*—Sandra L O'Shea
*Assistant Examiner*—James W Cranson
(74) *Attorney, Agent, or Firm*—Renner, Otto, Boisselle & Sklar, LLP

(57) ABSTRACT

A medical marker trackable by a medical navigation system includes a marker body and a luminescence agent within the marker body. The luminescence agent is operative to emit light without an electrical power supply coupled to the luminescence agent.

24 Claims, 2 Drawing Sheets

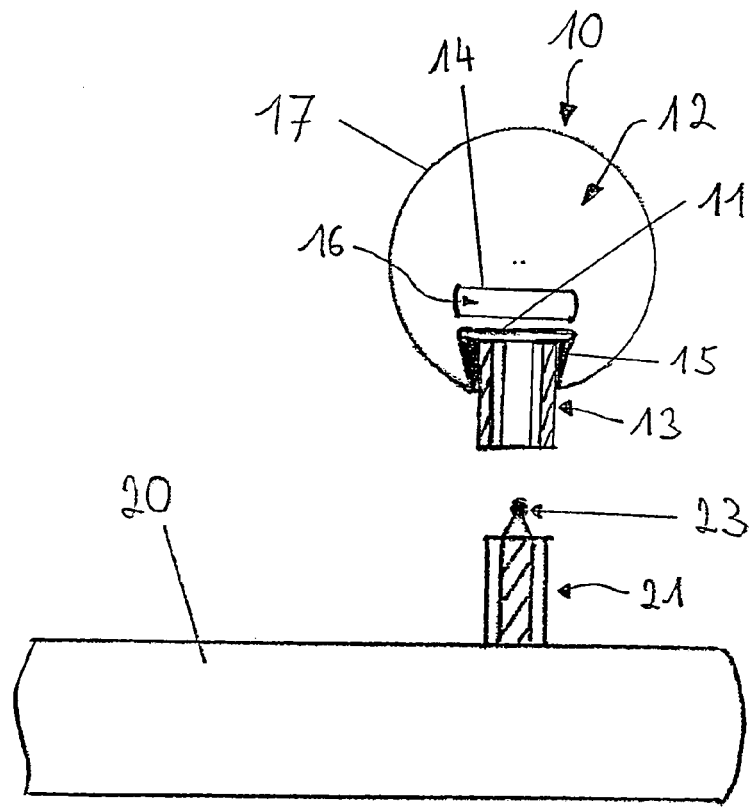
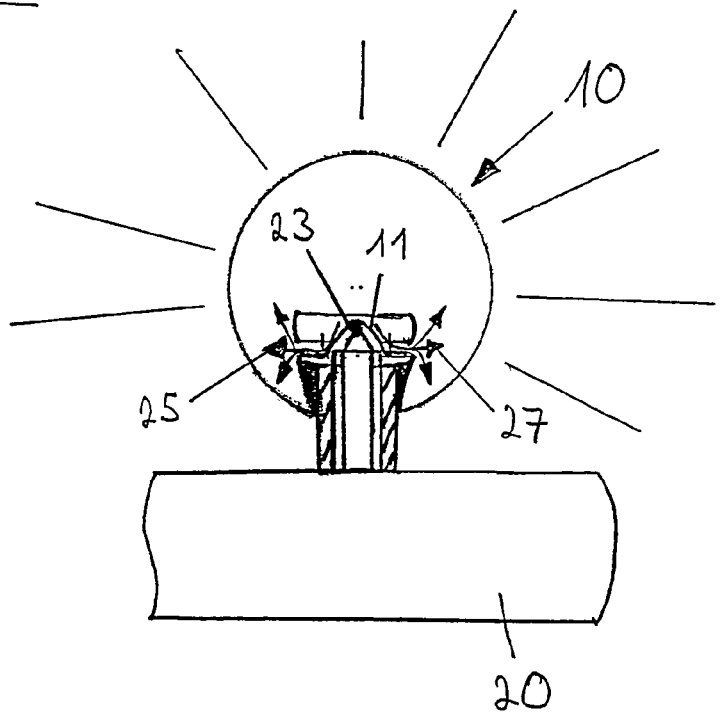
Fig. 1
Fig. 2

MEDICAL MARKER MEANS

RELATED APPLICATION DATA

This application claims priority of U.S. Provisional Application No. 60/738,546 filed on Nov. 21, 2005, which is incorporated herein by reference in its entirety.

FIELD OF THE INVENTION

The invention relates to medical markers and, more particularly, to a medical marker that utilizes a luminescence agent to emit a trackable signal.

BACKGROUND OF THE INVENTION

Active markers (e.g., LED markers) emit a trackable signal without the need for an external light source. Typically, such markers obtain power, for example, from an external power source via a cable connection or via an internal battery pack. Thus, instruments which are fitted with such active markers either have a cable attached thereto or are supplied with energy by batteries or power packs.

Cables can be problematic, as they tend to obstruct the work area and/or make it difficult to handle the markers and/or instrument. Batteries or power packs, on the other hand, can be heavy and/or difficult to sterilize. Further, active LED markers have the disadvantage of a narrow emitting angle.

Passive markers, such as are known for example from DE 196 39 615 A1, solve the handling and sterilization problems associated with active markers. However, manufacturing such passive markers can be relatively complicated, as a reflective covering generally is formed over such markers. Further, a significant amount of manual labor is involved in creating such markers.

SUMMARY OF THE INVENTION

The present invention provides a medical marker that includes a marker body which can be positionally detected by a medical localization or tracking system. The marker body includes a luminescence agent which can be illuminated without an electrical energy supply coupled to the agent and/or body. In other words, self-illuminating and/or cold-illuminating agents are utilized that enable the marker to illuminate from the material itself, without an energy supply provided by cable or batteries. Thus, costly manufacture of reflective coatings for the markers is not required. Further, the markers have good luminisity (e.g., good recognizability for the respective marker means), and sterilization of the markers is relatively easy compared to prior art active markers. Another advantage is that the infrared (IR) irradiation, which typically is included in a camera system for detecting passive markers, can be omitted. IR radiation generally requires significant power, generates heat, and occasionally can disrupt other operating apparatus, such as video recorder remote controls, operating table remote controls or finger pulsometers.

The term "luminescence" in the present context substantially means that the marker body can illuminate solely from the material or materials used, without needing an external energy supply (cable or connected batteries/power packs). The luminescence agent can be one which luminesces according to at least one of the following processes: chemoluminescence (a chemical reaction provides the energy to elevate electrons into higher energy states); photoluminescence (electrons are moved to the higher energy state by optical stimulation (irradiation)); electroluminescence (the emission of light is caused by applying an electric field); and/or radioluminescence (shooting particles into a suitable material in order to generate luminescence, for example electrons, alpha-particles).

In the following, the present description will deal mainly with the use of chemoluminescence. However, it is within the scope of the present invention to use other types of luminescence. For example, it is perfectly conceivable to irradiate the markers before use in a medical procedure with suitable amounts of light, to then position markers on instruments or treatment means and to use them over the period of time in which they re-emit the light energy (as for example the luminous numbers on a clock). Such marker may be used either as passive marker or as active marker, for example, within the scope of surgically navigating instruments and treatment means.

Chemoluminescence, as mentioned above, is a luminescence (e.g., the emission of light in the visible range or also the emission of ultraviolet or infrared light) associated with a chemical reaction. In chemoluminescence, the temperature is significantly below the incandescent temperature of the substances involved and, therefore, is called "cold light". This latter property makes chemoluminescence very suitable for medical applications, as it does not generate any disruptive, excess heat that has to be dissipated.

In chemoluminescence, electrical energy is converted into electronic or, more rarely, oscillation energy. This presupposes that said energy is released at once, i.e., not in numerous stages. Chemoluminescence occurs in numerous chemical processes in which high-energy, unstable intermediate stages are created and immediately decompose again. Although the reaction mechanism of many chemoluminescence reactions has not yet been conclusively explained, the principle of forming high-energy tetracyclic systems (dioxetanes) has in many cases been confirmed by experiments. Reacting oxygen ($O_2$), peroxides ($R_2O_2$), hyperoxides ($O_2$—) or hydroperoxides ($RO_2H$) with luminophores often creates dioxetanes, such as 1,2-dioxitanes or 1,2-dioxetes, which in turn decompose into two carbonyl compounds, wherein one of these is created in an electronically excited singlet or triplet state. The fragment in the electronically excited state can return to its ground state by emitting the energy in the form of photons. While the molecules in the excited singlet state quickly return to their ground state by emitting the characteristic fluorescent light, the excited triplet molecules are longer-lived. The phosphorescent light thus created in a substantially smaller yield barely contributes to a "usable" chemoluminescence.

One example of chemoluminescence is the so-called "luminol reaction", an example of an oxidation process in which the reaction energy is emitted not as heat but solely as light energy. The reaction is based on the oxidative release of nitrogen from phthalic acid hydrazide (luminol) by the action of alkali hydrogen peroxide. This reaction is catalysed by red prussiate of potash (hexacyanoferrate (III)). The luminescence can be triggered not only by hydrogen peroxide but also by ozone. In an alkali hydrogen peroxide solution, luminol shows a weak but sustained chemoluminescence, the intensity of which is strengthened by certain catalysts (potassium hexacyanoferrate (III), haemin), simultaneously reducing the decay time.

Chemoluminescence is also known from light sticks (snap light sticks), in which a glass ampoule contains hydrogen peroxide which is used as the oxidant for the reaction which illuminates the stick. When the breaking point in the ampoule is broken, the hydrogen peroxide is released into a solution containing oxalic phthalate ester. When this oxalic phthalate ester is oxidized to form phenol and carbon dioxide, the intermediate stage 1,2-dioxetane-3,4-dione is formed. This intermediate stage reacts with a dye molecule in the light stick, typically a diphenyl anthracene, and the dye molecule is electronically excited. In this excited state, it emits a photon and so generates its luminescence.

The chemoluminescences described above or similar chemoluminescences can thus be used in a marker, wherein the luminescence agent includes of a number of substances that are illuminated by being mixed, wherein the mixing itself can be separately triggered by a suitable triggering agent. On the other hand, there exists the possibility of using markers which comprise a fastening by which they can be attached to instruments or treatment means. In this case, the mixing of the substances could be triggered by activating or fixing the fastening. In this case, or also in cases in which mixing is triggered separately, the marker body can form a container for a first substance, in which another container is arranged that includes a second substance. The mixing of the substances then, for example, can be triggered by breaking the inner container. If the fastening described above is used, then fixing the marker can open a container including a first substance, which is situated within a space including a second substance.

For navigation and tracking systems, it is often advantageous for them to operate in the infrared range, such that disruptions from visible light can be minimized or eliminated. The luminescence agent can be a luminescence agent that emits in the infrared range. Furthermore, the luminescence agent can be an agent which solely or at least partially and preferably not glaringly emits in the range of visible light. The marker means can comprise an indicator which shows when the luminosity of the luminescence agent decreases or ebbs. The indicator can be the illuminating portion emitting in the range of visible light of a luminescence agent which otherwise emits in the infrared range. In other words, a marker body can be provided that includes a luminescence agent, wherein the luminescence agent can illuminate in the infrared range and also (to a minor extent) in the visible range across a limited wavelength. Wavelengths for IR light, for example, are 700 to 900 nm, especially 850 to 890 nm; visible light can be below 700 nm in wavelength. Chemoluminescent emitters which can emit in the infrared range, for example, would be CH3Se (750 to 825 nm in wavelength), IF (450 to 800 nm) and SF2 (550 to 875 nm). On the basis of the small portion of visible light, however, it would be possible to determine when the luminosity of the marker decreases or ebbs, and it could be replaced with a new marker.

The marker can comprise one or more marker bodies or a number of groups of marker bodies, wherein the luminescence agent of each marker may illuminate in a different color. In this example, the marker bodies or groups of marker bodies can be provided on and/or attached to an instrument or treatment means, color-coded and characteristic of the respective instrument or treatment means, wherein an instrument and/or treatment means can comprise marker bodies or groups of marker bodies in the same color or in different colors.

The marker body can form an insert which can be inserted into a receptacle of an instrument or treatment means, wherein translucent openings for the light emitted by the marker body are provided in or on the receptacle. Rod-shaped luminescent illuminating agents already available, for example, can be used for rod-shaped instruments. The translucent openings, which are inexpensive and simple to manufacture, can serve as the marker itself.

The invention is explained below in more detail on the basis of embodiments. It can comprise any of the features described here, individually and in any combination.

BRIEF DESCRIPTION OF THE DRAWINGS

The forgoing and other embodiments of the invention are hereinafter discussed with reference to the drawings.

FIG. 1 illustrates an exemplary luminescence marker in accordance with the invention, before being fastened to a surgical instrument.

FIG. 2 illustrates the marker of FIG. 1 fastened to an exemplary instrument.

DETAILED DESCRIPTION

Figure 3:
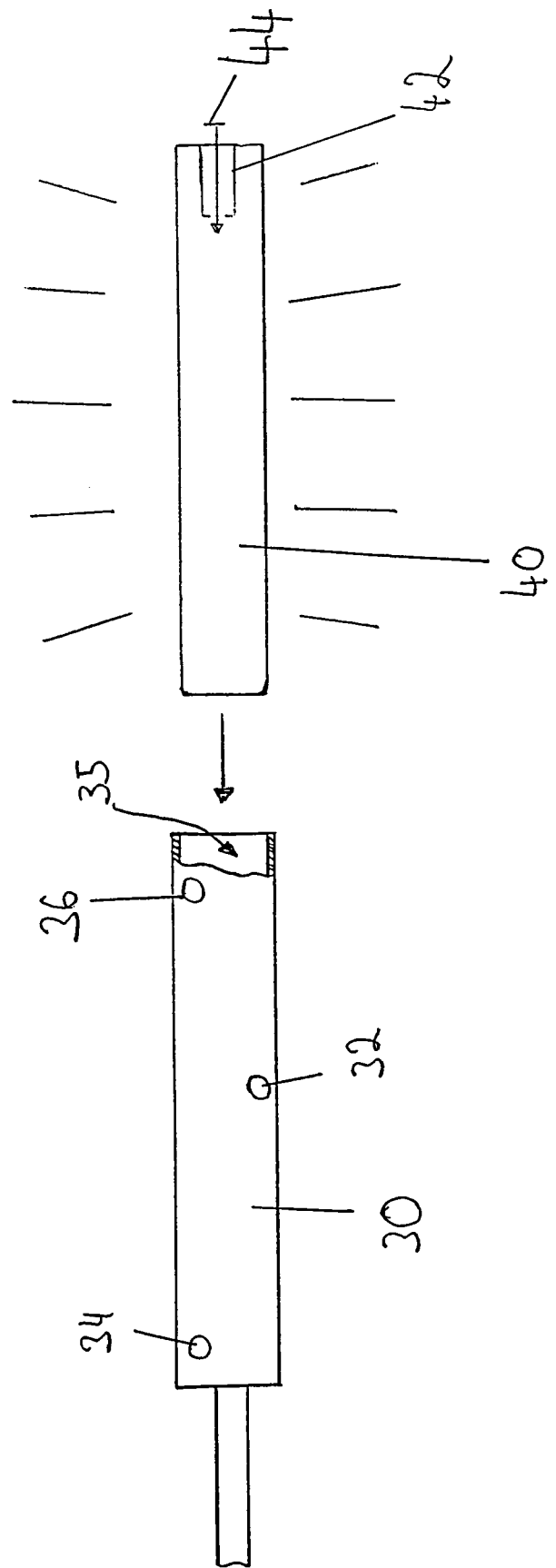
FIG. 3 illustrates an exemplary luminescence rod marker which can be inserted into an object, such as an instrument body.

FIGS. 1 and 2 illustrate an exemplary marker fastening system for attaching an exemplary marker 10 to a surgical instrument 20. The marker 10 can be formed in a spherical shape and includes a casing which is permeable to light and/or diffusely permeable to light. A spherical part 17 of the casing connects to a connecting piece 15, which in turn connects to a membrane 11. The parts 11, and 17 together form an enclosed space. The connecting piece 15 connects the casing to a first fastening part of a socket 13, said first fastening part including an inner thread which extends in a central inner through-bore. Furthermore, a capsule 14 made of a breakable material is also fixed over the membrane 11.

While a first liquid 12 is situated in the spherical casing 17, the capsule 14 carries a second liquid 16. The two liquids are substances which, when mixed together, generate a chemoluminescence and preferably emit mainly in the infrared range (around 860 to 890 nm). In addition, this radiation also can include a small portion of visible light. The substances described above, or any substances which those having ordinary skill in the art would regard as suitable, can be used.

A second fastening part, which in the present example is in the form of a protruding pin 21, includes an outer thread and is situated on a side of the surgical instrument 20, of which only a part of the handle can be seen. A breaking device is schematically indicated as a rounded tip 23 on an upper part of the pin 21.

FIG. 2 illustrates what happens when the first fastening part 13 of the marker 10 is attached (e.g., via threads) onto the second fastening part (i.e., pin 21). Once screwed on, the tip 23 protrudes beyond the upper edge of the socket 13 and extends the membrane 11 without damaging it. Through the membrane, the tip 23 destroys the breakable material of the capsule 14 such that the second liquid 16 can escape from the capsule 14 and mix with the first liquid 12 in the spherical marker. The escape of the liquid is indicated by the arrows 25 and 27 in FIG. 2. Mixing the liquids creates the luminescence, and the marker 10 can thus be used as a localization aid for the instrument 20 for the entire duration of luminescence. When the luminosity decreases or ebbs, the user sees this in the decrease and/or ebb of the visible light portion, and the marker can be exchanged by unscrewing it and replacing it with another. Because the membrane 11 is not destroyed when the ampoule 14 is broken, no liquid escapes from the inner space of the marker; the system remains "clean" and the markers can be provided as pre-sterilised disposable items.

FIG. 3 shows an exemplary instrument handle 30 which includes transit holes 32, 34, 36 at different points. The handle 30 is formed hollow elongated member, as can be seen from the partial cut-away shown at the receptacle 35.

A luminescent rod 40 can be inserted into the receptacle 35. The luminescent rod 40 in turn includes an enclosed inner space containing a first substance and a breakable ampoule 42 containing a second substance. An activating device is schematically indicated by the reference sign 44, using which the facing end of the ampoule 42 can be broken and the mixing of the substances and the luminescence can therefore be triggered.

Using the activating device 44, the mixing of the two liquids in the luminescent rod 40 can be triggered before it is inserted, and the rod 40 then can be inserted into the receptacle 35 of the handle 30 from behind. The rod 40 then shines by its luminescence through the translucent openings (holes) 32, 34 and 36 and, thus, provides a sort of marker array and/or group of markers including three openings which can be detected by a tracking system. Here, too, there is scope for individualizations. Each instrument can include characteristically arranged translucent openings, thereby enabling a tracking and/or navigation system to recognize and track the instrument. In this way, an identifiable surgical instrument including a marker array can be manufactured in a very simple way using a luminescent rod which is already commercially available.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical marker, comprising:
   a marker body; and
   a luminescence agent within the marker body, said luminescence agent operative to emit light without an electrical power supply coupled to the luminescence agent, wherein said marker is positionally trackable by a medical tracking system.

2. The marker according to claim 1, wherein the luminescence agent luminesces according to at least one of chemoluminescence, photoluminescence, electroluminescence or radioluminescence.

3. The marker according to claim 1, wherein the luminescence agent includes of a number of substances that illuminate when mixed together.

4. The marker according to claim 3, further comprising a fastening device, wherein when the fastening device is activated or fixed, mixing of the substances is triggered.

5. The marker according to claim 4, wherein fixing the fastening device opens a container including a first substance situated within a space including a second substance.

6. The marker according to claim 1, wherein the luminescence agent emits in the infrared range.

7. The marker according to claim 1, wherein the luminescence agent solely or at least partially emits in the range of visible light.

8. The marker according to claim 1, further comprising an indicator operative to show when the luminosity of the luminescence agent decreases or ebbs.

9. The marker according to claim 7, wherein the indicator comprises the illuminating portion of the luminescence agent emitting light in the visible light range and the infrared range.

10. The marker according to claim 1, further comprising a plurality of marker bodies or a plurality of groups of marker bodies, wherein the luminescence agent in each marker body illuminates in a different color in each group or body.

11. The marker according to claim 1, further comprising an instrument or treatment means attached to the marker body or to a group of marker bodies, said marker body or groups of marker bodies being color-coded and characteristic of the respective instrument or treatment means.

12. The marker according to claim 11, wherein the instrument comprises a plurality of marker bodies or groups of marker bodies in the same color.

13. The marker according to claim 11, wherein the instrument comprises a plurality of marker bodies or groups of marker bodies in different colors.

14. The marker according to claim 1, wherein the marker body forms an insert that is insertable into a receptacle of an instrument or treatment means, wherein translucent openings are provided in or on the receptacle to enable light emitted by the marker body to pass through instrument.

15. The marker according to claim 1, wherein said marker body comprises:
    an opening; and
    a deformable sealing member formed at said opening so as to create a closed space in the marker body.

16. The marker according to claim 15, further comprising a frangible capsule arranged in said marker body at said opening.

17. The marker according to claim 15, wherein said opening includes a threaded bore for attachment of the marker to a device.

18. The marker according to claim 1, wherein said marker emits light at an angle greater than 180 degrees.

19. A trackable instrument assembly, comprising:
    a medical instrument; and
    at least one light emitting device adapted to generate light via a luminescence agent, said light emitting device attached to said instrument,
    wherein said instrument assembly emits a characteristic pattern of light that is positionally trackable by a medical tracking system.

20. The instrument assembly according to claim 19, wherein said medical instrument includes a receptacle for receiving the at least one light emitting device, said receptacle including a plurality of translucent openings that enable light emitted by the light emitting device to pass therethrough.

21. The instrument assembly according to claim 20, wherein said openings are characteristically arranged so as to enable identification of the instrument by a medical tracking or navigation system.

22. The instrument assembly according to claim 19, wherein said medical instrument includes a marker attachment device adapted to cause the luminescence agent to emit light upon the marker being attached to the marker attachment device.

23. The instrument assembly according to claim 22, wherein said attachment device includes a threaded bore formed on the marker, and a threaded post formed on the medical instrument.

24. A method of tracking a medical instrument within a medical workspace, comprising:

emitting from the instrument a characteristic pattern of light, wherein said light is generated using a luminescence agent; and using a medical tracking system to positionally track the characteristic pattern of light emitted from the instrument.

* * * * *